(12) United States Patent
Choi et al.

(10) Patent No.: US 11,399,746 B2
(45) Date of Patent: Aug. 2, 2022

(54) PERSONALIZED BIO-INFORMATION CORRECTING APPARATUS AND METHOD

(71) Applicant: SAMSUNG ELECTRONICS CO., LTD., Suwon-si (KR)

(72) Inventors: Ka Ram Choi, Hwaseong-si (KR); So Young Lee, Daejeon (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 189 days.

(21) Appl. No.: 16/739,981

(22) Filed: Jan. 10, 2020

(65) Prior Publication Data
US 2020/0345281 A1  Nov. 5, 2020

(30) Foreign Application Priority Data

May 2, 2019 (KR) .................... 10-2019-0051645

(51) Int. Cl.
*A61B 5/145* (2006.01)
*G16H 50/50* (2018.01)
(Continued)

(52) U.S. Cl.
CPC .......... *A61B 5/14532* (2013.01); *A61B 5/681* (2013.01); *A61B 5/7221* (2013.01);
(Continued)

(58) Field of Classification Search
CPC . A61B 5/14532; A61B 5/7221; A61B 5/7235; A61B 5/14546; A61B 5/7278;
(Continued)

(56) References Cited

U.S. PATENT DOCUMENTS 9,149,232 B2 * 10/2015 Rodriguez-Llorente ..................
                                                    A61B 5/14552
9,213,010 B2    12/2015 Yang et al.
                        (Continued)

FOREIGN PATENT DOCUMENTS

EP    3 474 287 A1    4/2019
JP    2014-109984 A   6/2014
             (Continued)

OTHER PUBLICATIONS

Communication dated Sep. 25, 2020, issued by the European Patent Office in European Application No. 20170608.2.
(Continued)

*Primary Examiner* — Eric F Winakur
*Assistant Examiner* — Alice Ling Zou
(74) *Attorney, Agent, or Firm* — Sughrue Mion, PLLC

(57) ABSTRACT

A personalized bio-information correcting apparatus includes a communication interface configured to acquire original bio-information value data of a user, and a processor configured to obtain a personalized bio-information guideline, based on a personalized physiological model, identify whether at least one value among the acquired original bio-information value data is an outlier, based on the obtained personalized bio-information guideline, and based on the at least one value among the acquired original bio-information value data being identified to be the outlier, obtain final bio-information value data by correcting the at least one value among the acquired original bio-information value data.

26 Claims, 12 Drawing Sheets

(51) Int. Cl.
*G16H 10/60* (2018.01)
*G16H 20/10* (2018.01)
*A61B 5/00* (2006.01)

(52) U.S. Cl.
CPC ........... *A61B 5/7235* (2013.01); *G16H 10/60* (2018.01); *G16H 20/10* (2018.01); *G16H 50/50* (2018.01)

(58) Field of Classification Search
CPC .... A61B 5/7264; A61B 5/7203; G16H 50/50; G16H 50/20; G16H 50/00
See application file for complete search history.

(56) References Cited

U.S. PATENT DOCUMENTS

| | | | |
|---|---|---|---|
| 9,357,958 B2 | 6/2016 | Yang et al. | |
| 9,408,567 B2 | 8/2016 | Wang et al. | |
| 9,625,414 B2 | 4/2017 | Yang et al. | |
| 9,625,415 B2 | 4/2017 | Yang et al. | |
| 9,632,060 B2 | 4/2017 | Shah et al. | |
| 9,645,111 B2 | 5/2017 | Szyman et al. | |
| 9,801,576 B2 | 10/2017 | Yang et al. | |
| 9,808,191 B2 | 11/2017 | Yang et al. | |
| 9,861,746 B2 | 1/2018 | Gautham et al. | |
| 9,863,911 B2 | 1/2018 | Wang et al. | |
| 9,989,490 B2 | 6/2018 | Yang et al. | |
| 9,989,491 B2 | 6/2018 | Szyman et al. | |
| 10,123,749 B2 | 11/2018 | Kamimura | |
| 10,156,543 B2 | 12/2018 | Yang et al. | |
| 10,172,544 B2 | 1/2019 | Yang et al. | |
| 10,321,865 B2 | 6/2019 | Gautham et al. | |
| 10,335,076 B2 | 7/2019 | Wang et al. | |
| 10,335,077 B2 | 7/2019 | Wang et al. | |
| 10,342,468 B2 | 7/2019 | Wang et al. | |
| 11,058,358 B2 * | 7/2021 | Lee | A61B 5/7246 |
| 2003/0060692 A1 | 3/2003 | Ruchti et al. | |
| 2004/0133086 A1 * | 7/2004 | Ciurczak | A61B 5/1455 |
| | | | 600/322 |
| 2007/0032706 A1 * | 2/2007 | Kamath | A61B 5/14539 |
| | | | 600/300 |
| 2008/0287761 A1 * | 11/2008 | Hayter | A61B 5/0004 |
| | | | 600/365 |
| 2010/0280329 A1 * | 11/2010 | Randlov | G16H 50/50 |
| | | | 600/300 |
| 2011/0106011 A1 | 5/2011 | Cinar et al. | |
| 2013/0109944 A1 | 5/2013 | Sparacino et al. | |
| 2013/0328572 A1 | 12/2013 | Wang et al. | |
| 2013/0328573 A1 | 12/2013 | Yang et al. | |
| 2013/0328578 A1 | 12/2013 | Shah et al. | |
| 2013/0331672 A1 | 12/2013 | Szyman et al. | |
| 2013/0331673 A1 | 12/2013 | Gautham et al. | |
| 2013/0331674 A1 | 12/2013 | Yang et al. | |
| 2013/0331676 A1 | 12/2013 | Morgan et al. | |
| 2013/0332085 A1 | 12/2013 | Yang et al. | |
| 2014/0188402 A1 * | 7/2014 | Garcia | G01M 99/008 |
| | | | 702/23 |
| 2015/0268228 A1 | 9/2015 | Schulat et al. | |
| 2015/0289820 A1 * | 10/2015 | Miller | A61B 5/7207 |
| | | | 600/300 |
| 2015/0297144 A1 | 10/2015 | Kamimura | |
| 2015/0306314 A1 | 10/2015 | Doyle, III et al. | |
| 2016/0054424 A1 | 2/2016 | Yang et al. | |
| 2016/0252473 A1 | 9/2016 | Yang et al. | |
| 2016/0320338 A1 | 11/2016 | Wang et al. | |
| 2017/0049386 A1 * | 2/2017 | Abraham | G06N 7/005 |
| 2017/0127983 A1 | 5/2017 | Spegazzini et al. | |
| 2017/0164879 A1 | 6/2017 | Yang et al. | |
| 2017/0172474 A1 | 6/2017 | Yang et al. | |
| 2017/0176381 A1 | 6/2017 | Yang et al. | |
| 2017/0197030 A1 | 7/2017 | Szyman et al. | |
| 2017/0328861 A1 | 11/2017 | Wang et al. | |
| 2018/0020958 A1 | 1/2018 | Lee et al. | |
| 2018/0021515 A1 | 1/2018 | Yang et al. | |
| 2018/0074010 A1 | 3/2018 | Wang et al. | |
| 2018/0074011 A1 | 3/2018 | Wang et al. | |
| 2018/0074012 A1 | 3/2018 | Wang et al. | |
| 2018/0104410 A1 | 4/2018 | Gautham et al. | |
| 2018/0279928 A1 | 10/2018 | Bohm et al. | |
| 2018/0289333 A1 | 10/2018 | Kamath et al. | |
| 2019/0059793 A1 | 2/2019 | Yang et al. | |
| 2019/0059794 A1 | 2/2019 | Yang et al. | |
| 2019/0076068 A1 | 3/2019 | Yang et al. | |
| 2019/0110751 A1 | 4/2019 | Lee et al. | |
| 2019/0192768 A1 * | 6/2019 | Gupta | A61B 5/4839 |
| 2019/0269355 A1 | 9/2019 | Wang et al. | |
| 2019/0290172 A1 * | 9/2019 | Hadad | A61B 5/0022 |

FOREIGN PATENT DOCUMENTS

| | | | |
|---|---|---|---|
| JP | 2016-197108 A | 11/2016 | |
| KR | 10-2013-0142016 A | 12/2013 | |
| KR | 10-1600379 B1 | 3/2016 | |
| KR | 10-2017-0105647 A | 9/2017 | |
| KR | 10-2018-0009637 A | 1/2018 | |
| KR | 10-2019-0043034 A | 4/2019 | |
| WO | WO-0200112 A2 * | 1/2002 | ......... A61B 5/14532 |

OTHER PUBLICATIONS

Karam Choi et al., "A Computational Method to Determine Glucose Infusion Rates for Isoglycemic Intravenous Glucose Infusion Study", IEEE Journal of Biomedical and Health Informatics, Jan. 2016, vol. 20, No. 1, pp. 4-10 (7 pages total).

Staal et al., "Kalman Smoothing for Objective and Automatic Preprocessing of Glucose Data", IEEE Journal of Biomedical and Health Informatics, 2018, pp. 1-9, 9 pages total.

Sadikoglu et al., "Filtering continuous glucose monitoring signal using Savitzky-Golay filter and Simple Multivariate Thresholding", Procedia Computer Science, 102, 2016, pp. 342-350, 9 pages total.

* cited by examiner

PERSONALIZED BIO-INFORMATION CORRECTING APPARATUS AND METHOD

CROSS-REFERENCE TO RELATED APPLICATION

This application claims priority to Korean Patent Application No. 10-2019-0051645, filed on May 2, 2019, in the Korean Intellectual Property Office, the entire disclosure of which is incorporated herein by reference for all purposes.

BACKGROUND

1. Field

Example embodiments of the disclosure relate to correcting bio-information by taking into account an individual's physiological response.

2. Description of Related Art

Diabetes is a chronic disease that causes various complications and can be hardly cured, and hence people with diabetes are advised to check their blood glucose regularly to prevent complications. When insulin is administered to control blood glucose, the blood glucose levels may have to be closely monitored to avoid hypoglycemia and control insulin dosage.

Blood glucose response varies from individual to individual, even with the same food intake, depending on the individual's characteristics (e.g., age, sex, weight, region, race, and the like). Thus, to increase the accuracy of measuring a blood glucose level, such individual's characteristics may be taken into account.

SUMMARY

Example embodiments provide a personalized bio-information correcting apparatus and a personalized bio-information correcting method in which a personalized physiological model is generated by taking into account an individual's physiological response and is used to measure bio-information.

According to embodiments, a personalized bio-information correcting apparatus includes a communication interface configured to acquire original bio-information value data of a user, and a processor configured to obtain a personalized bio-information guideline, based on a personalized physiological model, identify whether at least one value among the acquired original bio-information value data is an outlier, based on the obtained personalized bio-information guideline, and based on the at least one value among the acquired original bio-information value data being identified to be the outlier, obtain final bio-information value data by correcting the at least one value among the acquired original bio-information value data.

The personalized physiological model may be a mathematical model.

The communication interface may be further configured to acquire model bio-information value data for obtaining the personalized physiological model. The processor may be further configured to obtain the personalized physiological model, based on the acquired model bio-information value data.

The model bio-information value data may be blood glucose data. The processor may be further configured to identify whether the blood glucose data is sufficient to obtain the personalized physiological model, and based on the blood glucose data being identified to be sufficient to obtain the personalized physiological model, obtain the personalized physiological model, based on the blood glucose data.

The processor may be further configured to identify whether the blood glucose data is sufficient to obtain the personalized physiological model, based on either one or both of an amount of the blood glucose data and a time period of collecting the blood glucose data.

The processor may be further configured to obtain an estimated bio-information value, based on the personalized physiological model, and obtain the personalized bio-information guideline, based on the obtained estimated bio-information value.

The processor may be further configured to obtain the personalized bio-information guideline as either one or both of a first range from a first value that is obtained by subtracting a predetermined value from the obtained estimated bio-information value to a second value that is obtained by adding the predetermined value to the obtained estimated bio-information value, and a second range from a first predetermined percent of the obtained estimated bio-information value to a second predetermined percent of the obtained estimated bio-information value.

The processor may be further configured to, based on the at least one value among the acquired original bio-information value data deviating from the obtained personalized bio-information guideline at a time point of measuring the at least one value among the acquired original bio-information value data, identify that the at least one value among the acquired original bio-information value data is the outlier.

The processor may be further configured to, based on the at least one value among the acquired original bio-information value data being greater than a maximum value of the obtained personalized bio-information guideline at the time point, correct the at least one value among the acquired original bio-information value data to be the maximum value of the obtained personalized bio-information guideline at the time point, and based on the at least one value among the acquired original bio-information value data being less than a minimum value of the obtained personalized bio-information guideline at the time point, correct the at least one value among the acquired original bio-information value data to be the minimum value of the obtained personalized bio-information guideline at the time point.

The processor may be further configured to obtain a reliability of the final bio-information value data, based on either one or both of whether the at least one value among the acquired original bio-information value data falls within the obtained personalized bio-information guideline and a degree by which the at least one value among the acquired original bio-information value data deviates from the obtained personalized bio-information guideline.

The processor may be further configured to obtain a reliability of the personalized bio-information correcting apparatus, based on a bio-information value correction history.

The processor may be further configured to determine that the reliability of the personalized bio-information correcting apparatus is low, as a number of times of correcting the acquired original bio-information value data increases.

The processor may be further configured to, based on the obtained reliability of the personalized bio-information correcting apparatus being less than or equal to a predetermined threshold value, update the personalized physiological model.

The acquired original bio-information value data may be blood glucose data.

According to embodiments, a personalized bio-information correcting method of a personalized bio-information correcting apparatus, includes acquiring original bio-information value data of a user, obtaining a personalized bio-information guideline, based on a personalized physiological model, identifying whether at least one value among the acquired original bio-information value data is an outlier, based on the obtained personalized bio-information guideline, and based on the at least one value among the acquired original bio-information value data being identified to be the outlier, obtaining final bio-information value data by correcting the at least one value among the acquired original bio-information value data.

The personalized physiological model may be a mathematical model.

The personalized bio-information correcting method may further include acquiring model bio-information value data for obtaining the personalized physiological model, and obtaining the personalized physiological model, based on the acquired model bio-information value data.

The model bio-information value data is blood glucose data. The personalized bio-information correcting method may further include identifying whether the blood glucose data is sufficient to obtain the personalized physiological model. The obtaining of the personalized physiological model may include, based on the blood glucose data being identified to be sufficient to obtain the personalized physiological model, obtaining the personalized physiological model, based on the blood glucose data.

The identifying of whether the blood glucose data is sufficient to obtain the personalized physiological model may include identifying whether the blood glucose data is sufficient to obtain the personalized physiological model, based on either one or both of an amount of the blood glucose data and a time period of collecting the blood glucose data.

The personalized bio-information correcting method may further include obtaining an estimated bio-information value, based on the personalized physiological model. The obtaining of the personalized bio-information guideline may include obtaining the personalized bio-information guideline, based on the obtained estimated bio-information value.

The obtaining of the personalized bio-information guideline may include obtaining the personalized bio-information guideline as either one or both of a first range from a first value that is obtained by subtracting a predetermined value from the obtained estimated bio-information value to a second value that is obtained by adding the predetermined value to the obtained estimated bio-information value, and a second range from a first predetermined percent of the obtained estimated bio-information value to a second predetermined percent of the obtained estimated bio-information value.

The identifying of whether the at least one value among the acquired original bio-information value data is the outlier may include, based on the at least one value among the acquired original bio-information value data deviating from the obtained personalized bio-information guideline at a time point of measuring the at least one value among the acquired original bio-information value data, identifying that the at least one value among the acquired original bio-information value data is the outlier.

The obtaining of the final bio-information value data may include, based on the at least one value among the acquired original bio-information value data being greater than a maximum value of the obtained personalized bio-information guideline at the time point, correcting the at least one value among the acquired original bio-information value data to be the maximum value of the obtained personalized bio-information guideline at the time point, and based on the at least one value among the acquired original bio-information value data being less than a minimum value of the obtained personalized bio-information guideline at the time point, correcting the at least one value among the acquired original bio-information value data to be the minimum value of the obtained personalized bio-information guideline at the time point.

The personalized bio-information correcting method may further include obtaining a reliability of the final bio-information value data, based on either one or both of whether the at least one value among the acquired original bio-information value data falls within the obtained personalized bio-information guideline and a degree by which the at least one value among the acquired original bio-information value data deviates from the obtained personalized bio-information guideline.

The personalized bio-information correcting method may further include obtaining reliability of the personalized bio-information correcting apparatus, based on a bio-information value correction history.

The obtaining of the reliability of the personalized bio-information correcting apparatus may include determining that the reliability of the personalized bio-information correcting apparatus is low, as a number of times of correcting the acquired original bio-information value data increases.

The personalized bio-information correcting method may further include, based on the obtained reliability of the personalized bio-information correcting apparatus being less than or equal to a predetermined threshold value, updating the personalized physiological model.

The acquired original bio-information value data may be blood glucose data.

According to embodiments, a personalized bio-information correcting apparatus includes a bio-sensor configured to measure a bio-information value of a user, and a processor configured to obtain a personalized bio-information guideline, based on a personalized physiological model, identify whether the measured bio-information value is an outlier, based on the obtained personalized bio-information guideline, and based on the measured bio-information value being identified to be the outlier, correct the measured bio-information value.

The personalized physiological model may be a mathematical model.

The processor may be further configured to, based on the measured bio-information value deviating from the obtained personalized bio-information guideline at a time point of measuring the bio-information value, identify that the measured bio-information value is the outlier.

The processor may be further configured to, based on the measured bio-information value being greater than a maximum value of the obtained personalized bio-information guideline at the time point, correct the measured bio-information value to be the maximum value of the obtained personalized bio-information guideline at the time point, and based on the measured bio-information value being less than a minimum value of the obtained personalized bio-information guideline at the time point, correct the measured bio-information value to be the minimum value of the obtained personalized bio-information guideline at the time point.

According to embodiments, a personalized bio-information correcting apparatus includes a bio-sensor configured to measure first bio-information value data of a user, and a processor configured to obtain a personalized physiological model, based on the measured first bio-information value data, and obtain a personalized bio-information guideline as a range from first values that are obtained by subtracting a predetermined value from each value of the obtained personalized physiological model to second values that are obtained by adding the predetermined value to each value of the obtained personalized physiological model. The biosensor is further configured to measure second bio-information value data of the user. The processor is further configured to identify whether at least one value among the measured second bio-information value data is outside the obtained personalized bio-information guideline, and based on the at least one value among the measured second bio-information value data being identified to be outside the obtained personalized bio-information guideline, correct the at least one value among the measured second bio-information value data.

The processor may be further configured to, based on the at least one value among the measured second bio-information value data being greater than a maximum value of the obtained personalized bio-information guideline at a time point of measuring the at least one value among the measured second bio-information value data, correct the at least one value among the measured second bio-information value data to be the maximum value of the obtained personalized bio-information guideline at the time point, and based on the at least one value among the measured second bio-information value data being less than a minimum value of the obtained personalized bio-information guideline at the time point, correct the at least one value among the measured second bio-information value data to be the minimum value of the obtained personalized bio-information guideline at the time point.

BRIEF DESCRIPTION OF THE DRAWINGS

The above and/or other aspects of the disclosure will become apparent and more readily appreciated from the following description of the example embodiments, taken in conjunction with the accompanying drawings, in which.

DETAILED DESCRIPTION

Figure 1:
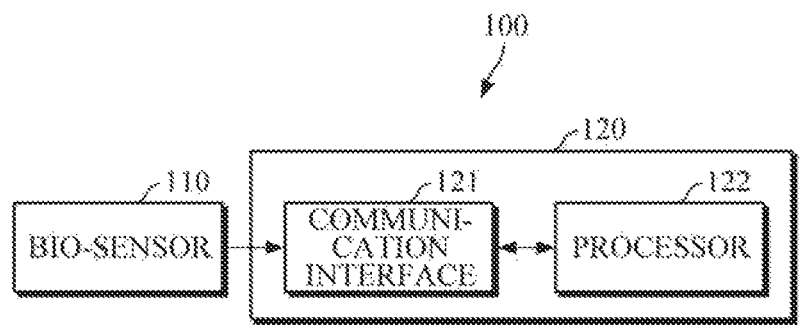
FIG. 1 is a block diagram illustrating a personalized bio-information measuring apparatus for measuring personalized bio-information according to an example embodiment.

Hereinafter, example embodiments of the disclosure will be described in detail with reference to the accompanying drawings. It may be noted that, in the drawings, the same reference symbols refer to same parts although illustrated in other drawings. In the following description, a detailed description of known functions and configurations incorporated herein will be omitted when it may obscure the subject matter of the disclosure.

Process steps described herein may be performed differently from a specified order, unless a specified order is clearly stated in the context of the disclosure. That is, each step may be performed in a specified order, substantially at the same time, in a reverse order, or in any other order.

Further, the terms used throughout this specification are defined in consideration of the functions according to embodiments, and can be varied according to a purpose of a user or manager, or precedent and so on. Therefore, definitions of the terms may be made on the basis of the overall context.

It will be understood that, although the terms "first," "second," etc. may be used herein to describe various elements, these elements may not be limited by these terms. These terms do not necessarily imply order, preference, or precedence and are only used to distinguish one element from another. Any references to singular may include plural unless expressly stated otherwise in the present specification, it may be understood that the terms, such as "including" or "having," etc., are intended to indicate the existence of the features, numbers, steps, actions, components, parts, or combinations thereof disclosed in the specification, and are not intended to preclude the possibility that one or more other features, numbers, steps, actions components, parts, or combinations thereof may exist or may be added.

Further, components that will be described in the specification are discriminated according to functions mainly performed by the components. That is, two or more components that will be described later can be integrated into a single component. Furthermore, a single component that will be explained later can be separated into two or more components. Moreover, each component that will be described can additionally perform some or all of a function executed by another component in addition to the main function thereof. Some or all of the main function of each component that will be explained can be carried out by another component. Each component may be implemented as hardware (e.g., a circuit, a microchip, a processor, etc.), software (e.g., instructions, code, a program, an application, firmware, etc.), or a combination of both.

FIG. 1 is a block diagram illustrating a personalized bio-information measuring apparatus for measuring personalized bio-information according to an example embodiment. A personalized bio-information measuring apparatus 100 of FIG. 1 may be an apparatus for measuring user's bio-information by taking into account a physiological response of the user, which may be mounted in an electronic device or be formed as a separate apparatus surrounded by a housing. The electronic device may include a mobile phone, a smartphone, a tablet computer, a notebook computer, a personal digital assistant (PDA), a portable multimedia player (PMP), a navigation device, an MP3 player, a digital camera, a wearable device, and the like. Examples of the wearable device may include a watch-type device, wristband-type device, a ring-type device, a waist belt-type device, a necklace-type device, an ankle band-type device, a thigh band-type device, a forearm band-type device, and the like. However, the electronic device is not limited to these examples, and the wearable device is neither limited to the above examples.

Here, the bio-information may be a concentration of an in vivo analyte and may include glucose, triglycerides, urea, uric acid, lactate, proteins, cholesterol, antioxidants (e.g., vitamins, carotenoids, flavonoids, ascorbic acid, tocopherol, and the like), ethanol, and the like, but is not limited thereto. In the case in which the in vivo analyte is glucose, the bio-information may be blood glucose. Hereinafter, embodiments in which the bio-information is blood glucose will be described for convenience of description.

Referring to FIG. 1, the personalized bio-information measuring apparatus 100 may include a bio-sensor 110 and a personalized bio-information correcting apparatus 120.

The bio-sensor 110 may measure a blood glucose level of the user. According to an example embodiment, the bio-sensor 110 may include both an invasive bio-sensor and a non-invasive bio-sensor. The non-invasive bio-sensor may include an optical-based sensor (e.g., near infrared (NIR) spectroscopy-based bio-sensor, a Raman spectroscopy-based bio-sensor, a photoplethysmography (PPG)-based bio-sensor, and the like), an impedance-based sensor, an ultrasound-based sensor, an acoustic sound-based sensor, and the like, but is not limited thereto. That is, the bio-sensor 110 is not limited in size and type as long as it is capable of measuring a blood glucose level of an object.

The personalized bio-information correcting apparatus 120 may determine a blood glucose guideline personalized based on a personalized physiological model (i.e., a personalized bio-information guideline) and correct the user's blood glucose level, which is measured through the bio-sensor 110, using the personalized blood glucose guideline. To this end, the personalized bio-information correcting apparatus 120 may include a communication interface 121 and a processor 122.

The communication interface 121 may acquire blood glucose level data (hereinafter referred to as blood glucose level data for use in model generation) to be used for generating a personalized physiological model from the bio-sensor 110. Also, the communication interface 121 may acquire blood glucose level data (hereinafter referred to as original blood glucose level data) to be used for determining a final blood glucose level using the personalized physiological model from the communication interface 121.

According to an example embodiment, the communication interface 121 may receive the blood glucose level data for use in model generation and the original blood glucose level data from the bio-sensor 110 using a wired or wireless communication technology. In this case, the wireless communication technology may include a Bluetooth communication, a Bluetooth low energy (BLE) communication, a near field communication (NFC), a wireless local area network (WLAN) communication, a ZigBee communication, an infrared data association (IrDA) communication, a Wi-Fi direct communication, an ultra-wideband (UWB) communication, Ant+ communication, a Wi-Fi communication, a radio frequency identification (RFID) communication, $3^{rd}$ generation (3G) communication, 4G communication, and 5G communication, but is not limited thereto.

When the blood glucose level data for use in model generation sufficient to generate a personalized physiological model is acquired, the processor 122 may generate a personalized physiological model using the acquired blood glucose level data for use in model generation. At this time, whether or not the blood glucose level data for use in model generation sufficient to generate a personalized physiological model is acquired may be determined by taking into account the amount of data, the data collection period, or the like. The personalized physiological model may be a blood glucose model as a mathematical model reflecting a user's personal physiological characteristic, and the personalized blood glucose guideline may indicate a blood glucose tolerance range of the user that is determined on the basis of the personalized physiological model.

According to an example embodiment, the personalized physiological model may be represented by Equations 1 to 3.

$$\frac{dG}{dt} = \begin{cases} \frac{Ra_{GutG}}{V} + \frac{Hepbal_G}{V} - k_1 G^{1.3} - k_2 I + \\ \quad \gamma \frac{dI}{dt}, & G \le 10 \text{ mmol}/L \\ \frac{Ra_{GutG}}{V} + \frac{Hepbal_G}{V} - k_1 G^{1.3} - k_2 I, \\ \quad \gamma \frac{dI}{dt} - \frac{k_3 G - k_4}{V}, & G > 10 \text{ mmol}/L \end{cases} \quad (1)$$

Here, G denotes a concentration of glucose, $Ra_{GutG}$ denotes a rate of glucose uptake into the mesenteric circulation, V denotes a parameter (e.g., 20% of a user's weight) related to a user's weight, $Hepbal_G$ denotes a hepatic glucose balance that reflects the sum of glucose generation in the liver and the glucose uptake from the mesenteric circulation, I denotes a concentration of insulin, γ denotes a control parameter of insulin for glucose, $k_1$ denotes a parameter indicating non-insulin mediated glucose uptake, $k_2$ denotes a parameter indicating insulin-mediated glucose uptake, and $k_3$ and $k_4$ denote, respectively, a slope and an intercept of renal glucose clearance.

The concentration of insulin I may be represented by Equation 2 to reflect an influence of a hormone (e.g., incretin or glucagon) related to the glucose control and insulin secretion on the secretion of insulin.

$$\frac{dI}{dt} = k_7 G^{1.3} + k_8 h - k_9 I + \beta \quad (2)$$

Here, $k_7$ and $k_8$ denote rates of insulin appearance for glucose and hormones, respectively, $k_9$ denotes an insulin clearance rate, β denotes an effect of an additional regulator. i.e., an effect of other factors except for glucose and hormones, and h denotes a concentration of hormone.

The concentration of hormone h may be represented by Equation 3 on the basis of the concentration of glucose-dependent insulinotropic polypeptide (GIP).

$$\frac{dh}{dt} = \frac{Ra_h}{V} + k_5 Duod_G - k_6 h \quad (3)$$

Here, $Ra_h$ denotes an appearance rate of incretin, $Duod_G$ denotes a rate of glucose delivery to the duodenum, $k_5$ denotes an appearance rate of hormone due to the duodenum, and $k_6$ denotes a hormone clearance rate.

The processor 122 may generate a personalized physiological model that reflects the user's personal physiological characteristic by optimizing parameters of Equations 1 to 3 on the basis of the acquired blood glucose level data for use in model generation.

The processor 122 may use the personalized physiological model to determine the personalized blood glucose guideline that reflects the user's personal physiological characteristic. According to an example embodiment, the processor 122 may determine the personalized blood glucose guideline to be one or a combination of a range from a value obtained by subtracting a predetermined value from an estimated blood glucose level obtained based on the personalized physiological model and a value obtained by adding the predetermined value to the estimated blood glucose level and a range from a predetermined percent of the estimated blood glucose level to another predetermined percent of the estimated blood glucose level.

For example, the personalized blood glucose guideline may be represented by one of Equations 4 to 7.

$$\text{guideline} = (I_{max}(t), I_{min}(t)) = (G_m(t) + a, G_m(t) - a) \tag{4}$$

$$\text{guideline} = (I_{max}(t), I_{min}(t)) = ((1-b)*G_m(t), (1+b)*G_m(t)) \tag{5}$$

$$\text{guideline} = \tag{6}$$
$$(I_{max}(t), I_{min}(t)) = \begin{cases} (G_m(t) + a, G_m(t) - a), & \text{if } G_m(t) < c \\ ((1-b)*G_m(t), (1+b)*G_m(t)), & \text{else} \end{cases}$$

$$\text{guideline} = \tag{7}$$
$$(I_{max}(t), I_{min}(t)) = \begin{cases} ((1-b)*G_m(t), (1+b)*G_m(t)), & \text{if } G_m(t) < c \\ (G_m(t) + a, G_m(t) - a), & \text{else} \end{cases}$$

Here, $I_{max}(t)$ and $I_{min}(t)$ denote a maximum value and a minimum value of the personalized blood glucose guideline at time t, respectively, $G_m(t)$ denotes an estimated blood glucose level at time t determined using the personalized physiological model, a denotes an absolute value that determines the range of the personalized blood glucose guideline, b denotes a ratio that determines the range of the personalized blood glucose guideline, and c denotes a reference blood glucose level. For example, a may be 15 mg/dL, b may be 0.15, and c may be 100 mg/dL, but they are not limited to these examples.

When the processor 122 acquires original blood glucose level data from the bio-sensor 110, the processor 122 may determine whether the original blood glucose level is an outlier using the personalized blood glucose guideline. According to an example embodiment, the processor 122 may map the original blood glucose level measurement time point to the personalized blood glucose guideline on the basis of a time point at which the user takes food and determine whether the original blood glucose level falls within a range of the personalized blood glucose guideline at the corresponding time point. When the original blood glucose level falls out of the range of the personalized blood glucose guideline at the corresponding time point, the processor 122 may determine the blood glucose level to be an outlier.

When the original blood glucose level is determined to be an outlier, the processor 122 may correct the original blood glucose level and determine the corrected blood glucose level to be a final blood glucose level. According to an example embodiment, the processor 122 may use a maximum value or a minimum value of the personalized blood glucose guideline at the corresponding time point to correct the original blood glucose level, which is determined to be an outlier. For example, when the original blood glucose level is greater than the maximum value of the personalized blood glucose guideline at the corresponding time point, the processor 122 may correct the original blood glucose level to the maximum value of the personalized blood glucose guideline at the corresponding time point, and may correct the original blood glucose level to the minimum value of the personalized blood glucose guideline of the corresponding time point when the original blood glucose level is smaller than the minimum value of the personalized blood glucose guideline at the corresponding time point.

When it is determined that the original blood glucose level is not an outlier, the processor 122 may determine the original blood glucose level to be a final blood glucose level.

According to an example embodiment, the processor 122 may recognize the user's food intake. For example, the processor 122 may recognize food intake by receiving an input of the user or may recognize the user's food intake on the basis of a sensor value of an intake recognition sensor installed inside or outside of the personalized bio-information correcting apparatus 120. In this case, the intake recognition sensor may include both a sensor that recognizes food intake through the movements of the mouth, larynx, throat, and the like and a sensor that recognizes food intake through the physiological changes. For example, the intake recognition sensor may include various types of sensors implemented in such a manner to recognize the sound of food intake, to capture an image of food, to recognize the movement of an arm, to detect swallowing, to recognize chest breathing, to measure a change in body temperature, to measure a change in blood flow, or the like, but is not limited thereto.

The processor 122 may determine the reliability of a final blood glucose level on the basis of whether the original blood glucose level falls within the personalized blood glucose guideline and the degree by which the original blood glucose level deviates from the personalized blood glucose guideline. For example, the processor 122 may determine that the reliability of the final blood glucose level is high when the original blood glucose level is within the personalized blood glucose guideline. Also, the processor 122 may determine that the reliability of the final blood glucose level is low when the original blood glucose level is out of the personalized blood glucose guideline and the degree of deviation is large.

The processor 122 may determine the reliability of the personalized bio-information correcting apparatus 120 itself on the basis of a blood glucose level correction history. For example, as the number of times of correcting the blood glucose level increases, the processor 122 may determine that the reliability of the personalized bio-information correcting apparatus 120 is low.

Also, the processor 122 may update the personalized physiological model and the personalized blood glucose guideline when the reliability of the personalized bio-information correcting apparatus 120 is lower than or equal to a predetermined threshold value. In this case, all or part of the blood glucose level data accumulated until present may be used or new blood glucose level data for use in model generation may be acquired from the bio-sensor 110 and be used.

Figure 2:
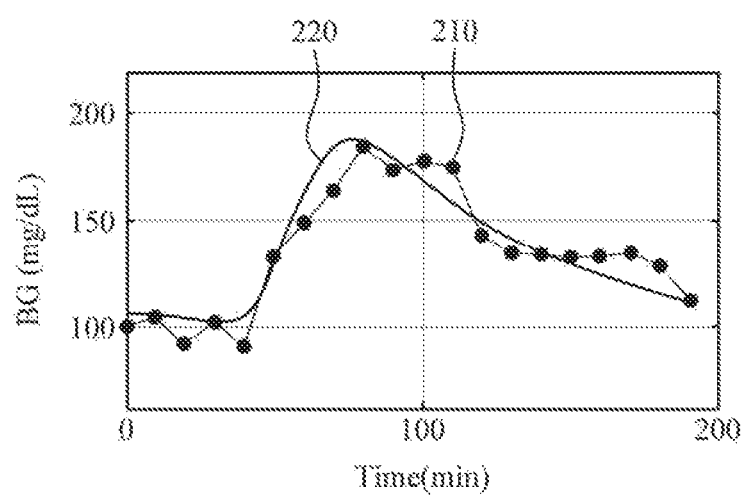
FIG. 2 is a graph for describing generating a personalized physiological model, using blood glucose level data for use in model generation.
Figure 3:
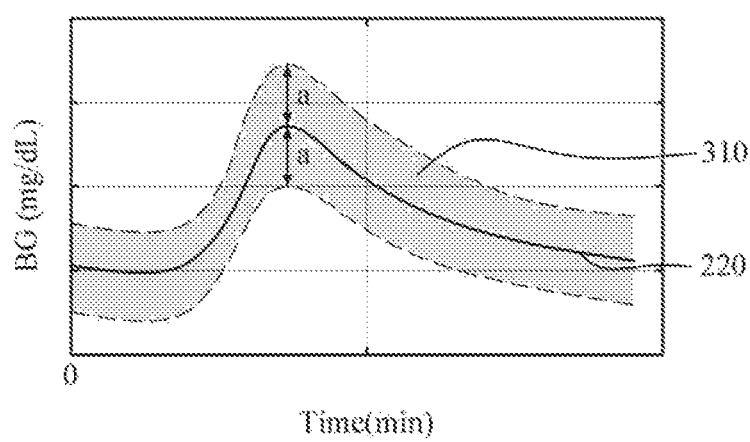
FIG. 3 is a graph for describing determination of a personalized blood glucose guideline, based on the personalized physiological model of FIG. 2.
Figure 4:
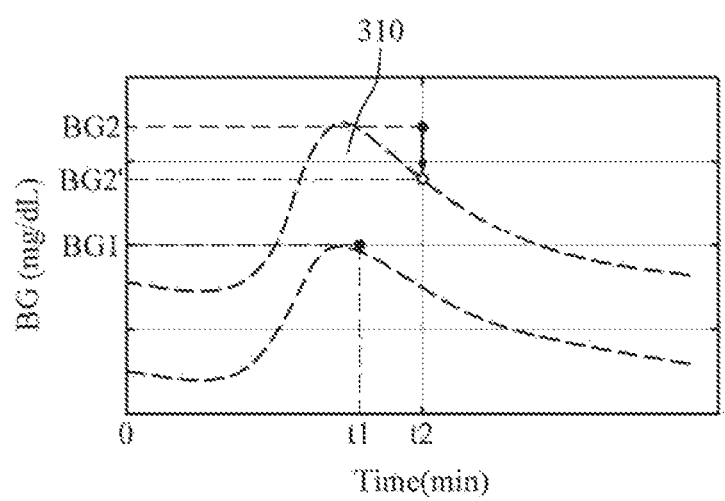
FIG. 4 is a graph for describing correction of an original blood glucose level, using the personalized blood glucose guideline of FIG. 3.

FIG. 2 is a graph for describing generating a personalized physiological model, using blood glucose level data for use in model generation. FIG. 3 is a graph for describing determination of a personalized blood glucose guideline, based on the personalized physiological model of FIG. 2. FIG. 4 is a graph for describing correction of an original blood glucose level, using the personalized blood glucose guideline of FIG. 3.

Referring to FIGS. 1 and 2, the processor 122 may generate a personalized physiological model 220 on the basis of blood glucose (BG) level data 210 for use in model generation acquired from the bio-sensor 110. In this case, the processor 122 may use Equations 1 to 3 described above.

Referring to FIGS. 1 and 3, the processor 122 may determine a personalized blood glucose guideline 310 using the personalized physiological model 220. For example, as shown in FIG. 3, the processor 122 may determine the personalized blood glucose guideline 310 to be a range from a value obtained by subtracting a predetermined value a from the estimated blood glucose level based on the personalized physiological model and a value obtained by adding the predetermined value a to the estimated blood glucose level. This may be expressed by Equation 4.

Referring to FIGS. 1 and 4, when the processor 122 acquires original blood glucose level data BG1 measured at a time point when time t1 elapses after food intake from the bio-sensor 110, the processor 122 may match a time point of measuring an original blood glucose level to t=t1 of the personalized blood glucose guideline that is a time point at which time t1 elapses from the time point (t=0) at which the user takes food, and may determine whether the original blood glucose level BG1 is within the range of the personalized blood glucose guideline at the corresponding time point (t=t1). The processor 122 may determine the original blood glucose level BG1 to be a final blood glucose level because the original blood glucose level BG1 is within the range of the personalized blood glucose guideline at the corresponding time point t=t1.

In addition, when the processor 122 acquires original blood glucose level data BG2 measured at a time point when time t2 elapses after food intake from the bio-sensor 110, the processor 122 may match a time point of measuring the original blood glucose level to t=t2 of the personalized blood glucose guideline that is a time point when time t2 elapses from a time point (t=0) at which the user takes food, and may determine whether the original blood glucose level BG2 falls within a range of the personalized blood glucose guideline at the corresponding time point (t=t2). Because the original blood glucose level BG2 falls out of the range of the personalized blood glucose guideline at the corresponding time point (t=t2), the processor 122 may correct the original blood glucose level BG2 to a maximum value BG2' of the personalized blood glucose guideline at the corresponding time point and determine the corrected blood glucose level BG2' to be a final blood glucose level.

Figure 5:
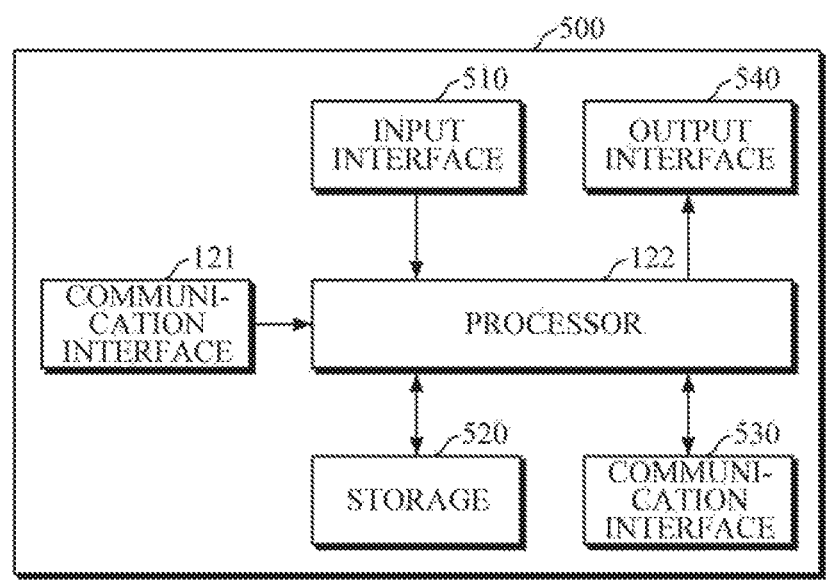
FIG. 5 is a block diagram illustrating another example of a personalized bio-information correcting apparatus according to an example embodiment.

FIG. 5 is a block diagram illustrating another example of a personalized bio-information correcting apparatus according to an example embodiment. A personalized bio-information correcting apparatus 500 of FIG. 5 may be embodiments of the personalized bio-information correcting apparatus 120 of FIG. 1. The personalized bio-information correcting apparatus may be configured to be mounted in an electronic device or to be a separate apparatus surrounded by a housing. The electronic device may include a mobile phone, a smartphone, a tablet computer, a notebook computer, a PDA, a PMP, a navigation device, an MP3 player, a digital camera, a wearable device, and the like. Examples of the wearable device may include a watch-type device, wristband-type device, a ring-type device, a waist belt-type device, a necklace-type device, an ankle band-type device, a thigh band-type device, a forearm band-type device, and the like. However, the electronic device is not limited to these examples, and the wearable device is neither limited to the above examples.

Referring to FIG. 5, the personalized bio-information correcting apparatus 500 may include the communication interface 121, the processor 122, an input interface 510, a storage 520, a communication interface 530, and an output interface 540. Here, the communication interface 121 and the processor 122 are substantially the same or similar to those described with reference to FIGS. 1 to 5, and thus detailed descriptions thereof will not be reiterated.

The input interface 510 may receive various operation signals from a user. According to embodiments, the input interface 510 may include a keypad, a dome switch, a touchpad, a jog wheel, a jog switch, a hardware (H/W) button, and the like. When a touchpad has a layered structure with a display, this structure may be referred to as a touch screen.

Programs or instructions for operation of the personalized bio-information correcting apparatus 500 may be stored in the storage 520 and the input data, the measured data, the processed data, and the like of the personalized bio-information correcting apparatus 500 may be stored therein. The storage 520 may include at least one type of storage medium, such as a flash memory type, a hard disk type, a multimedia card micro type, a card type memory (e.g., SD or XD memory) random access memory (RAM), static random access memory (SRAM), read-only memory (ROM), electrically erasable programmable read-only memory (EEPROM), programmable read-only memory (PROM), a magnetic memory, a magnetic disk, and an optical disk. In addition, the personalized bio-information correcting apparatus 500 may operate an external storage medium, such as a web storage that performs the storage function of the storage 520 on the Internet.

The communication interface 530 may communicate with an external device. For example, the communication interface 530 may transmit the input data, the stored data, the measured data, the processed data, and the like of the personalized bio-information correcting apparatus 500 to the external device, or receive a variety of data to estimate bio-information from the external device.

In this case, the external device may be medical equipment using the input data, the stored data, the processed data, and the like of the personalized bio-information correcting apparatus 500, a printer to print out results, or a display device to display the results. In addition, the external device may be a digital TV, a desktop computer, a mobile phone, a smartphone, a tablet computer, a notebook computer, a PDA, a PMP, a navigation device, an MP3 player, a digital camera, a wearable device, or the like, but is not limited thereto.

The communication interface 530 may communicate with the external device using Bluetooth communication, BLE communication, NFC, WLAN communication, ZigBee communication, IrDA communication, WFD communication, UWB communication, Ant+ communication, Wi-Fi communication, RFID communication, 3G communication, 4G communication, 5G communication, and the like. However, these are examples, and the type of communication is not limited thereto.

The output interface 540 may output the input data, the stored data, the measured data, the processed data, and the like of the personalized bio-information correcting apparatus 500. According to embodiments, the output interface 540 may output the input data, the stored data, the measured data, the processed data, and the like of the personalized bio-information correcting apparatus 500 using any one or any combination of an acoustic method, a visual method, and a tactile method. To this end, the output interface 540 may include a display, a speaker, a vibrator, and the like.

Figure 6:
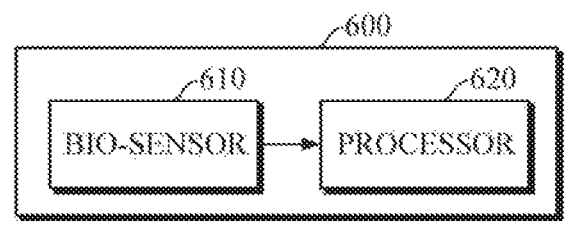
FIG. 6 is a block diagram illustrating still another example of a personalized bio-information correcting apparatus according to an example embodiment.

FIG. 6 is a block diagram illustrating still another example of a personalized bio-information correcting apparatus according to an example embodiment. The personalized bio-information correcting apparatus 600 of FIG. 6 may include a bio-sensor 610, unlike the personalized bio-information correcting apparatus 120 of FIG. 1. In the embodiments of FIG. 6, a processor 620 may directly control the bio-sensor 610 to measure a blood glucose level of a user. That is, the processor 620 may control the bio-sensor 610 to measure a blood glucose level of the user, thus acquiring blood glucose level data for use in model generation and original blood glucose level data.

The personalized bio-information correcting apparatus 600 may be configured to be mounted in an electronic device or to be a separate apparatus surrounded by a housing. The electronic device may include a mobile phone, a smartphone, a tablet computer, a notebook computer, a PDA, a PMP, a navigation device, an MP3 player, a digital camera, a wearable device, and the like. Examples of the wearable device may include a watch-type device, wristband-type device, a ring-type device, a waist belt-type device, a necklace-type device, an ankle band-type device, a thigh band-type device, a forearm band-type device, and the like. However, the electronic device is not limited to these examples, and the wearable device is neither limited to the above examples.

Figure 7:
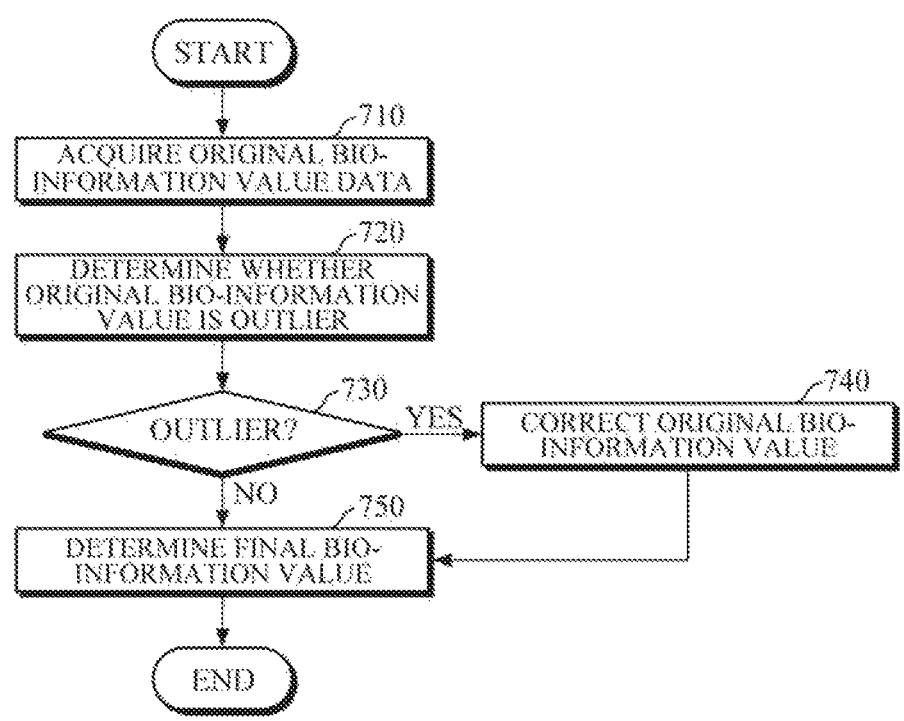
FIG. 7 is a flowchart illustrating a method of correcting bio-information according to an example embodiment.

FIG. 7 is a flowchart illustrating a method of correcting bio-information according to an example embodiment. The method of FIG. 7 may be performed by the personalized bio-information correcting apparatus 120, 500, or 600 of FIG. 1, 5, or 6.

Referring to FIG. 7, in operation 710, a personalized bio-information correcting apparatus may acquire original bio-information value data. For example, the personalized bio-information correcting apparatus may acquire original bio-information value data from a bio-sensor installed inside or outside of the personalized bio-information correcting apparatus.

In operation 720, the personalized bio-information correcting apparatus may determine whether the original bio-information value is an outlier using a personalized bio-information guideline. For example, the personalized bio-information correcting apparatus may match a time point of measuring the original bio-information value to the personalized bio-information guideline on the basis of a time point at which the user takes food, and may determine whether the original bio-information value falls within a range of the personalized bio-information guideline at the corresponding time point. Also, when the original bio-information value falls out of the range of the personalized bio-information guideline at the corresponding time point, the personalized bio-information correcting apparatus may determine the original bio-information value to be an outlier.

In operation 730, when it is determined that the original bio-information value is an outlier, in operation 740, the personalized bio-information correcting apparatus may correct the original bio-information value. According to embodiments, the personalized bio-information correcting apparatus may correct the original bio-information value, which is determined to be an outlier, to a maximum value or a minimum value of the personalized bio-information guideline at the corresponding time point that corresponds to the time point of measuring the original bio-information value. For example, when the original bio-information value is greater than the maximum value of the personalized bio-information guideline at the corresponding time point, the personalized bio-information correcting apparatus may correct the original bio-information value to the maximum value of the personalized bio-information guideline at the corresponding time point, and when the original bio-information value is smaller than the minimum value of the personalized bio-information guideline at the corresponding time point, may correct the original bio-information value to the minimum value of the personalized bio-information guideline at the corresponding time point.

In operation 750, the personalized bio-information correcting apparatus may determine the corrected bio-information value to be a final bio-information value.

In operation 730, when it is determined that the original bio-information value is not an outlier, in operation 750, the personalized bio-information correcting apparatus may determine the original bio-information value to be a final bio-information value.

Figure 8:
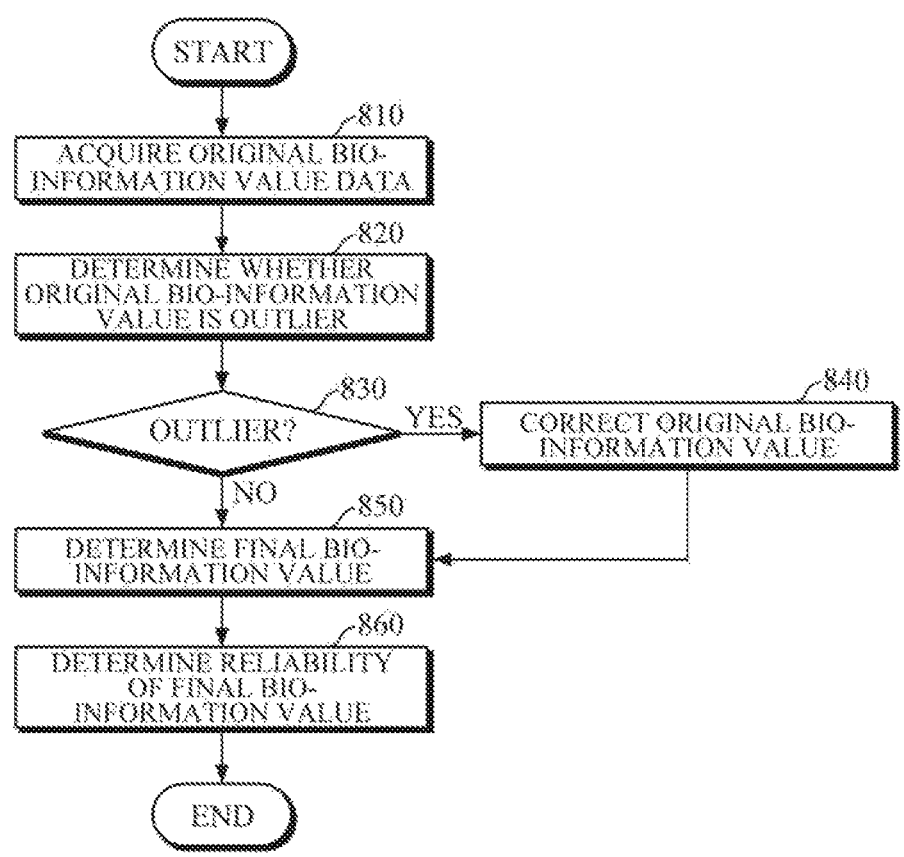
FIG. 8 is a flowchart illustrating another example of a method of correcting bio-information according to an example embodiment.

FIG. 8 is a flowchart illustrating another example of a method of correcting bio-information according to an example embodiment. The method of FIG. 8 may be performed by the personalized bio-information correcting apparatus 120, 500, or 600 of FIG. 1, 5, or 6. Operations 810, 820, 830, 840, and 850 of FIG. 8 are substantially the same as operations 710, 720, 730, 740, and 750 of FIG. 7, respectively, and thus these operations will be described in brief.

Referring to FIG. 8, a personalized bio-information correcting apparatus acquires original bio-information value data in operation 810, and determine whether an original bio-information value is an outlier using a personalized bio-information guideline in operation 820.

In operation 830, when it is determined that the original bio-information value is an outlier, the personalized bio-information correcting apparatus may correct the original bio-information value in operation 840, and determine the corrected bio-information value to be a final bio-information value in operation 850.

In operation 830, when it is determined that the original bio-information value is not an outlier, the personalized bio-information correcting apparatus may determine the original bio-information value to a final bio-information value in operation 850.

In operation 860, the personalized bio-information correcting apparatus may determine the reliability of the final bio-information value on the basis of whether the original bio-information value falls within the personalized bio-information guideline and the degree by which the original bio-information value deviates from the personalized bio-information guideline. For example, when the original bio-information value falls within the personalized bio-information guideline, the personalized bio-information correcting apparatus may determine that the reliability of the final bio-information value is high when the original bio-information value is within the personalized bio-information guideline. Also, the personalized bio-information apparatus may determine that the reliability of the final bio-information value is low when the original bio-information value is out of the personalized bio-information guideline and the degree of deviation is large.

Figure 9:
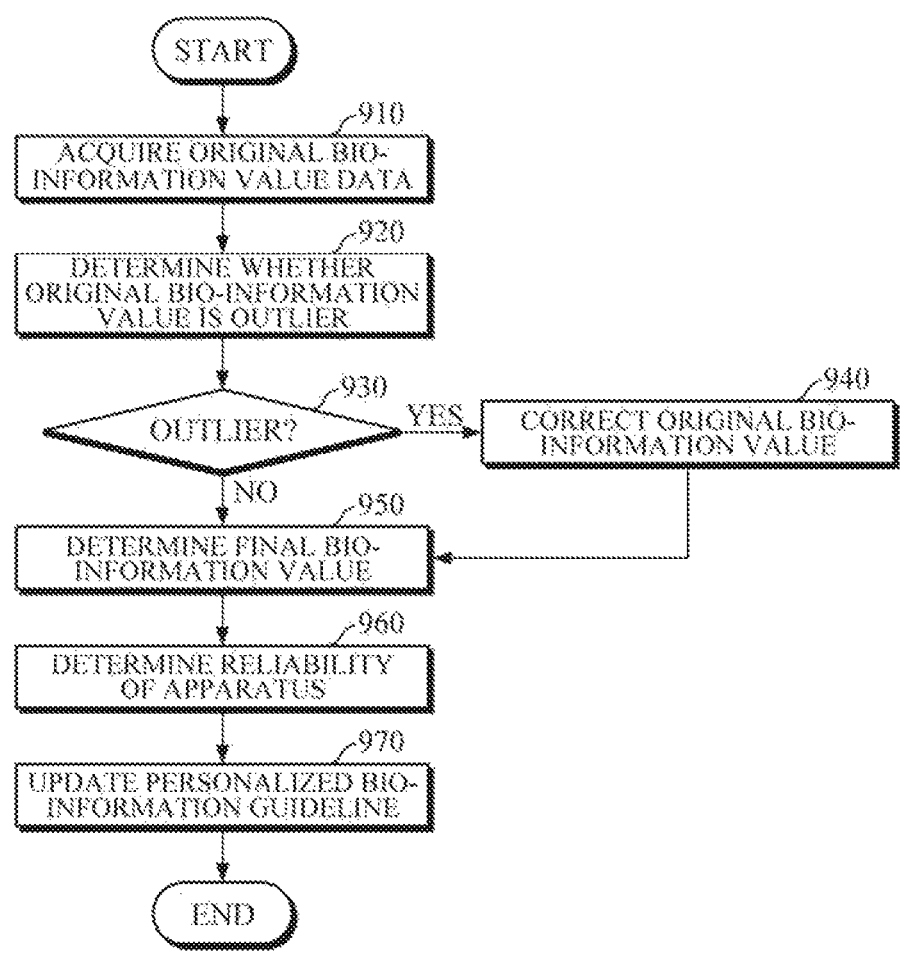
FIG. 9 is a flowchart illustrating still another example of a method of correcting bio-information according to an example embodiment.

FIG. 9 is a flowchart illustrating still another example of a method of correcting bio-information according to an example embodiment. The method of FIG. 9 may be performed by the personalized bio-information correcting apparatus 120, 500, or 600 of FIG. 1, 5, or 6. Operations 910, 920, 930, 940, and 950 of FIG. 9 are substantially the same as operations 710, 720, 730, 740, and 750 of FIG. 7, respectively, and thus these operations will be described in brief.

Referring to FIG. 9, a personalized bio-information correcting apparatus may acquire original bio-information value data in operation 910, and may determine whether the original bio-information value is an outlier using a personalized bio-information guideline in operation 920.

In operation 930, when it is determined that the original bio-information value is an outlier, the personalized bio-information correcting apparatus may correct the original bio-information value in operation 940, and determine the corrected bio-information value to be a final bio-information value in operation 950.

In operation 930, when it is determined that the original bio-information value is not an outlier, the personalized bio-information correcting apparatus may determine the original bio-information value to a final bio-information value in operation 950.

In operation 960, the personalized bio-information correcting apparatus may determine the reliability of the personalized bio-information correcting apparatus itself on the basis of a bio-information value correction history. For example, as the number of times of correcting the bio-information value increases, the personalized bio-information correcting apparatus may determine that its own reliability is low.

In operation 970, the personalized bio-information correcting apparatus may update a personalized physiological model and the personalized bio-information guideline when the reliability of the personalized bio-information correcting apparatus itself is lower than or equal to a predetermined threshold. In this case, the personalized bio-information correcting apparatus may use all or part of the bio-information value data accumulated until present or acquire and use new bio-information value data for use in model generation from an internally or externally installed bio-sensor.

Figure 10:
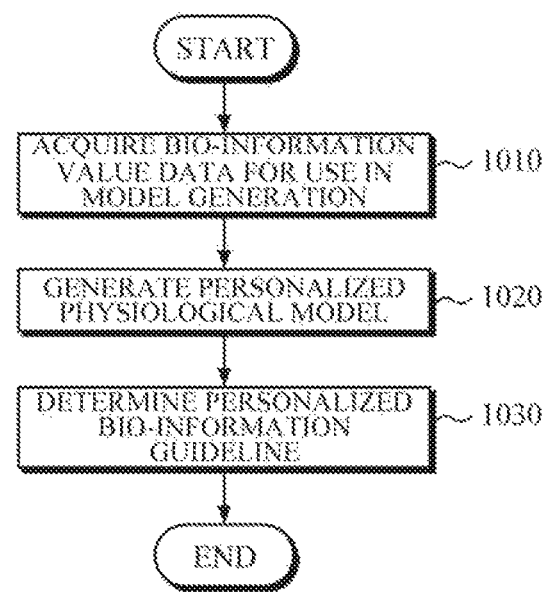
FIG. 10 is a flowchart illustrating a method of generating a personalized bio-information guideline according to an example embodiment.

FIG. 10 is a flowchart illustrating a method of generating a personalized bio-information guideline according to an example embodiment. The method of FIG. 10 may be performed by the personalized bio-information correcting apparatus 120, 500, or 600 of FIG. 1, 5, or 6.

Referring to FIG. 10, in operation 1010, a personalized bio-information correcting apparatus may acquire bio-information value data for use in model generation from an internally or externally installed bio-sensor.

When bio-information value data for use in model generation sufficient to generate a personalized physiological model is acquired, in operation 1020, the personalized bio-information correcting apparatus may generate a personalized physiological model using the acquired bio-information value data for use in model generation. For example, the personalized bio-information correcting apparatus may generate the personalized physiological model that reflects a user's personal physiological characteristic by optimizing parameters of Equations 1 to 3 on the basis of the acquired bio-information value data for use in model generation.

In operation 1030, the personalized bio-information correcting apparatus may determine a personalized bio-information guideline that reflects the user's personal physiological characteristic using the personalized physiological model. According to embodiments, the personalized bio-information correcting apparatus may determine the personalized bio-information guideline using any one or any combination of Equations 4 to 7.

Figure 11:
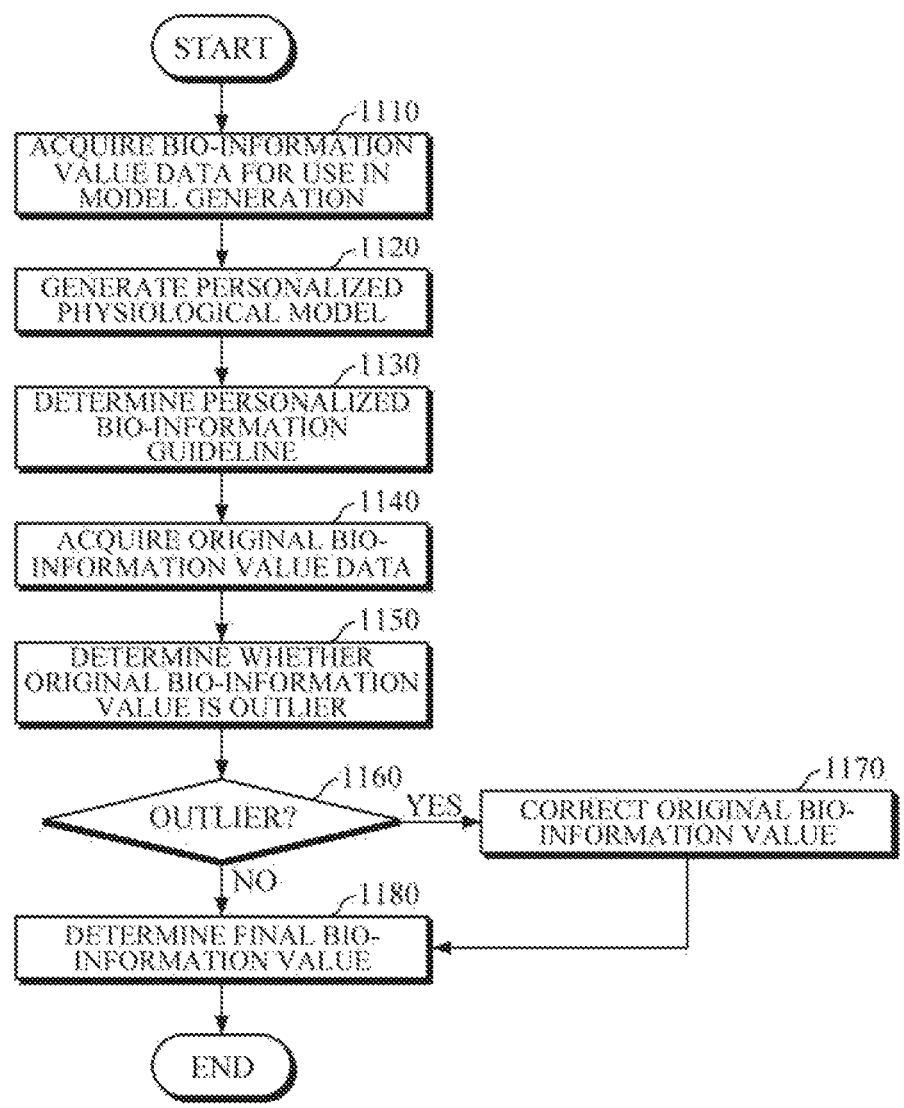
FIG. 11 is a flowchart illustrating yet another example of a method of correcting bio-information according to an example embodiment.

FIG. 11 is a flowchart illustrating yet another example of a method of correcting bio-information according to an example embodiment. The method of FIG. 11 may be performed by the personalized bio-information correcting apparatus 120, 500, or 600 of FIG. 1, 5, or 6. Operations 1110, 1120, and 1130 of FIG. 11 are substantially the same as operations 1010, 1020, and 1030 of FIG. 10, respectively, and operations 1140, 1150, 1160, 1170, and 1180 are substantially the same as operations 710, 720, 730, 740, and 750 of FIG. 7, respectively, and thus these operations will be described in brief.

Referring to FIG. 11, a personalized bio-information correcting apparatus may acquire bio-information value data for use in model generation in operation 1110, generate a personalized physiological model using the acquired bio-information value data for use in model generation in operation 1120, and determine a personalized bio-information guideline using the personalized physiological model in operation 1030.

The personalized bio-information correcting apparatus may acquire original bio-information value data in operation 1140 and determine whether an original bio-information value is an outlier using the personalized bio-information guideline in operation 1150.

In operation 1160, when it is determined that the original bio-information value is an outlier, the personalized bio-information correcting apparatus may correct the original bio-information value in operation 1170, and determine the corrected bio-information value to be a final bio-information value in operation 1180.

In operation 1160, when it is determined that the original bio-information value is not an outlier, the personalized bio-information correcting apparatus may determine the original bio-information value to be a final bio-information value in operation 1180.

Figure 12:
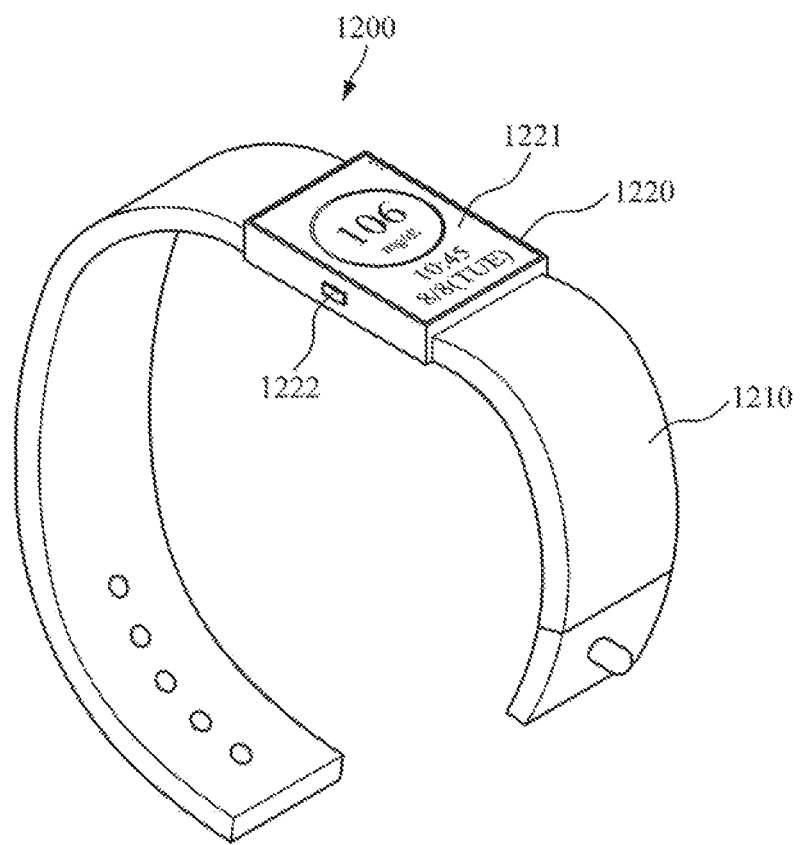
FIG. 12 is a diagram illustrating a wrist wearable device according to an example embodiment.

FIG. 12 is a diagram illustrating a wrist wearable device according to an example embodiment.

Referring to FIG. 12, a wrist wearable device 1200 may include a strap 1210 and a main body 1220.

The strap 1210 may be formed as two sections that are connected at both sides of the main body 1220 to be fastened to each other, or may be integrally formed as a smart band. The strap 1210 may be made of a flexible material to bend around a user's wrist so that the main body 1220 may be worn around the user's wrist.

The above-described personalized bio-information correcting apparatus 120, 500, or 600 may be mounted inside the main body 1220. Also, a battery may be equipped in the main body 1220 to supply power to the wrist wearable device 1200 and the personalized bio-information correcting apparatus 120, 500, or 600.

A bio-sensor may be mounted on a lower part of the main body 1220 to be exposed to a wrist of a user. In this manner, when the user wears the wrist wearable device 1200, the bio-sensor may naturally come into contact with the user's skin.

The wrist wearable device 1200 may further include a display 1221 and an input interface 1222 that are mounted in the main body 1220. The display 1221 may display the processed data, the processing result data, and the like of the wrist wearable device 1200 and the personalized bio-information correcting apparatus 120, 500, or 600. The input interface 1222 may receive various operation signals from the user.

The current embodiments can be implemented as computer readable codes in a computer readable record medium. Codes and code segments constituting the computer program can be easily inferred by a skilled computer programmer in the art. The computer readable record medium includes all types of record media in which computer readable data are stored. Examples of the computer readable record medium include a ROM, a RAM, a CD-ROM, a magnetic tape, a floppy disk, and an optical data storage. Further, the record medium may be implemented in the form of a carrier wave such as Internet transmission. In addition, the computer readable record medium may be distributed to computer systems over a network, in which computer readable codes may be stored and executed in a distributed manner.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A personalized bio-information correcting apparatus comprising:
    a processor configured to:
        acquire model bio-information value data of a user;
        obtain a personalized physiological model for the user based on the model bio-information value data;
        determine a personalized bio-information guideline based on the personalized physiological model; and
    a communication interface configured to acquire original bio-information value data of the user, wherein the processor is further configured to:
    identify whether at least one value among the original bio-information value data is an outlier, based on the personalized bio-information guideline; and
    based on the at least one value among the original bio-information value data being identified to be the outlier, obtain final bio-information value data by correcting the at least one value among the original bio-information value data,
    wherein the processor is further configured to determine, based on a bio-information value correction history, that a reliability of the personalized bio-information correcting apparatus is low based on an increased number of times of correcting the original bio-information value data, and
    wherein the processor is further configured to, based on the reliability of the personalized bio-information correcting apparatus being less than or equal to a predetermined threshold value, update the personalized physiological model by using new model bio-information value data of the user.

2. The personalized bio-information correcting apparatus of claim 1, wherein the personalized physiological model is a mathematical model.

3. The personalized bio-information correcting apparatus of claim 1, wherein the model bio-information value data is blood glucose data, and
    wherein the processor is further configured to:
        identify whether the blood glucose data is sufficient to obtain the personalized physiological model; and
        based on the blood glucose data being identified to be sufficient to obtain the personalized physiological model, obtain the personalized physiological model, based on the blood glucose data.

4. The personalized bio-information correcting apparatus of claim 3, wherein the processor is further configured to identify whether the blood glucose data is sufficient to obtain the personalized physiological model, based on either one or both of an amount of the blood glucose data and a time period of collecting the blood glucose data.

5. The personalized bio-information correcting apparatus of claim 1, wherein the processor is further configured to:
    obtain an estimated bio-information value, based on the personalized physiological model; and
    determine the personalized bio-information guideline, based on the estimated bio-information value.

6. The personalized bio-information correcting apparatus of claim 5, wherein the processor is further configured to determine the personalized bio-information guideline as either one or both of a first range from a first value that is obtained by subtracting a predetermined value from the estimated bio-information value to a second value that is obtained by adding the predetermined value to the estimated bio-information value, and a second range from a first predetermined percent of the estimated bio-information value to a second predetermined percent of the estimated bio-information value.

7. The personalized bio-information correcting apparatus of claim 1, wherein the processor is further configured to, based on the at least one value among the original bio-information value data deviating from the personalized bio-information guideline at a time point of measuring the at least one value among the original bio-information value data, identify that the at least one value among the original bio-information value data is the outlier.

8. The personalized bio-information correcting apparatus of claim 7, wherein the processor is further configured to:
    based on the at least one value among the original bio-information value data being greater than a maximum value of the personalized bio-information guideline at the time point, correct the at least one value among the original bio-information value data to be the maximum value of the personalized bio-information guideline at the time point; and
    based on the at least one value among the original bio-information value data being less than a minimum value of the personalized bio-information guideline at the time point, correct the at least one value among the original bio-information value data to be the minimum value of the personalized bio-information guideline at the time point.

9. The personalized bio-information correcting apparatus of claim 1, wherein the processor is further configured to obtain a reliability of the final bio-information value data, based on either one or both of whether the at least one value among the original bio-information value data falls within the personalized bio-information guideline and a degree by which the at least one value among the original bio-information value data deviates from the personalized bio-information guideline.

10. The personalized bio-information correcting apparatus of claim 1, wherein the original bio-information value data is blood glucose data.

11. A personalized bio-information correcting method of a personalized bio-information correcting apparatus, the personalized bio-information correcting method comprising:
- acquiring model bio-information value data of a user;
- obtaining a personalized physiological model for the user based on the model bio-information value data;
- determining a personalized bio-information guideline based on the personalized physiological model;
- acquiring original bio-information value data of the user;
- identifying whether at least one value among the original bio-information value data is an outlier, based on the personalized bio-information guideline;
- based on the at least one value among the original bio-information value data being identified to be the outlier, obtaining final bio-information value data by correcting the at least one value among the original bio-information value data;
- determining, based on a bio-information value correction history, that a reliability of the personalized bio-information correcting apparatus is low based on an increased number of times of correcting the original bio-information value data, and
- based on the reliability of the personalized bio-information correcting apparatus being less than or equal to a predetermined threshold value, updating the personalized physiological model by using new model bio-information value data of the user.

12. The personalized bio-information correcting method of claim 11, wherein the personalized physiological model is a mathematical model.

13. The personalized bio-information correcting method of claim 11, wherein the model bio-information value data is blood glucose data,
- wherein the personalized bio-information correcting method further comprises identifying whether the blood glucose data is sufficient to obtain the personalized physiological model, and
- wherein the obtaining of the personalized physiological model comprises, based on the blood glucose data being identified to be sufficient to obtain the personalized physiological model, obtaining the personalized physiological model, based on the blood glucose data.

14. The personalized bio-information correcting method of claim 13, wherein the identifying of whether the blood glucose data is sufficient to obtain the personalized physiological model comprises identifying whether the blood glucose data is sufficient to obtain the personalized physiological model, based on either one or both of an amount of the blood glucose data and a time period of collecting the blood glucose data.

15. The personalized bio-information correcting method of claim 11, further comprising obtaining an estimated bio-information value, based on the personalized physiological model,
- wherein the obtaining of the personalized bio-information guideline comprises obtaining the personalized bio-information guideline, based on the estimated bio-information value.

16. The personalized bio-information correcting method of claim 15, wherein the determining of the personalized bio-information guideline comprises determining the personalized bio-information guideline as either one or both of a first range from a first value that is obtained by subtracting a predetermined value from the estimated bio-information value to a second value that is obtained by adding the predetermined value to the estimated bio-information value, and a second range from a first predetermined percent of the estimated bio-information value to a second predetermined percent of the estimated bio-information value.

17. The personalized bio-information correcting method of claim 11, wherein the identifying of whether the at least one value among the original bio-information value data is the outlier comprises, based on the at least one value among the original bio-information value data deviating from the obtained personalized bio-information guideline at a time point of measuring the at least one value among the original bio-information value data, identifying that the at least one value among the original bio-information value data is the outlier.

18. The personalized bio-information correcting method of claim 17, wherein the obtaining of the final bio-information value data comprises:
- based on the at least one value among the original bio-information value data being greater than a maximum value of the personalized bio-information guideline at the time point, correcting the at least one value among the original bio-information value data to be the maximum value of the personalized bio-information guideline at the time point; and
- based on the at least one value among the original bio-information value data being less than a minimum value of the personalized bio-information guideline at the time point, correcting the at least one value among the original bio-information value data to be the minimum value of the personalized bio-information guideline at the time point.

19. The personalized bio-information correcting method of claim 11, further comprising obtaining a reliability of the final bio-information value data, based on either one or both of whether the at least one value among the original bio-information value data falls within the personalized bio-information guideline and a degree by which the at least one value among the original bio-information value data deviates from the personalized bio-information guideline.

20. The personalized bio-information correcting method of claim 11, wherein the original bio-information value data is blood glucose data.

21. A personalized bio-information correcting apparatus comprising:
- a processor configured to:
  - acquire model bio-information value data of a user;
  - obtain a personalized physiological model for the user based on the model bio-information value data;
  - determine a personalized bio-information guideline based on the personalized physiological model; and
- a bio-sensor configured to measure a bio-information value of the user,
- wherein the processor is further configured to:
  - identify whether the measured bio-information value is an outlier, based on the personalized bio-information guideline; and
  - based on the measured bio-information value being identified to be the outlier, correct the measured bio-information value,
- wherein the processor is further configured to determine, based on a bio-information value correction history, that a reliability of the personalized bio-information correcting apparatus is low based on an increased number of times of correcting the measured bio-information value, and
- wherein the processor is further configured to, based on the reliability of the personalized bio-information correcting apparatus being less than or equal to a predetermined threshold value, update the personalized personalized physiological model by using new model bio-information value data of the user.

22. The personalized bio-information correcting apparatus of claim 21, wherein the personalized physiological model is a mathematical model.

23. The personalized bio-information correcting apparatus of claim 21, wherein the processor is further configured to, based on the measured bio-information value deviating from the obtained personalized bio-information guideline at a time point of measuring the bio-information value, identify that the measured bio-information value is the outlier.

24. The personalized bio-information correcting apparatus of claim 23, wherein the processor is further configured to:
based on the measured bio-information value being greater than a maximum value of the personalized bio-information guideline at the time point, correct the measured bio-information value to be the maximum value of the personalized bio-information guideline at the time point; and
based on the measured bio-information value being less than a minimum value of the personalized bio-information guideline at the time point, correct the measured bio-information value to be the minimum value of the personalized bio-information guideline at the time point.

25. A personalized bio-information correcting apparatus comprising:
a bio-sensor configured to measure first bio-information value data of a user; and
a processor configured to:
obtain a personalized physiological model for the user, based on the measured first bio-information value data;
determine a personalized bio-information guideline as a range from first values that are obtained by subtracting a predetermined value from each value of the personalized physiological model to second values that are obtained by adding the predetermined value to each value of the personalized physiological model,
wherein the bio-sensor is further configured to measure second bio-information value data of the user,
wherein the processor is further configured to:
identify whether at least one value among the measured second bio-information value data is outside the personalized bio-information guideline; and
based on the at least one value among the measured second bio-information value data being identified to be outside the personalized bio-information guideline, correct the at least one value among the measured second bio-information value data,
wherein the processor is further configured to determine, based on a bio-information value correction history, that a reliability of the personalized bio-information correcting apparatus is low based on an increased number of times of correcting the measured second bio-information value data, and
wherein the processor is further configured to, based on the reliability of the personalized bio-information correcting apparatus being less than or equal to a predetermined threshold value, update the personalized physiological model by using new model bio-information value data of the user.

26. The personalized bio-information correcting apparatus of claim 25, wherein the processor is further configured to:
based on the at least one value among the measured second bio-information value data being greater than a maximum value of the personalized bio-information guideline at a time point of measuring the at least one value among the measured second bio-information value data, correct the at least one value among the measured second bio-information value data to be the maximum value of the personalized bio-information guideline at the time point; and
based on the at least one value among the measured second bio-information value data being less than a minimum value of the personalized bio-information guideline at the time point, correct the at least one value among the measured second bio-information value data to be the minimum value of the personalized bio-information guideline at the time point.

* * * * *